(12) United States Patent
Schraga (10) Patent No.: US 7,575,583 B1
(45) Date of Patent: *Aug. 18, 2009

(54) SINGLE USE LANCET DEVICE (76) Inventor: Steven Schraga, 1841 NE. 146th St., North Miami, FL (US) 33181

(*) Notice: Subject to any disclaimer, the term of this patent is extended or adjusted under 35 U.S.C. 154(b) by 400 days.

This patent is subject to a terminal disclaimer.

(21) Appl. No.: 11/249,178

(22) Filed: Oct. 11, 2005

Related U.S. Application Data (63) Continuation of application No. 10/171,464, filed on Jun. 13, 2002, now Pat. No. 6,958,072, which is a continuation of application No. 09/709,738, filed on Nov. 10, 2000, now Pat. No. 6,514,270.

(60) Provisional application No. 60/297,826, filed on Jun. 13, 2001.

(51) Int. Cl.
A61B 17/14 (2006.01)
(52) U.S. Cl. ..................... 606/182; 606/161
(58) Field of Classification Search ............... 606/181, 606/182, 183, 184, 185; 600/583
See application file for complete search history.

(56) References Cited

U.S. PATENT DOCUMENTS

| 55,775 | A | 6/1866 | Klee |
| 931,791 | A | 8/1909 | Niergarth |
| 2,711,738 | A | 6/1955 | Kelly et al. |
| 3,358,689 | A | 12/1967 | Higgins |
| 3,483,810 | A | 12/1969 | Peters et al. |
| 3,760,809 | A | 9/1973 | Campbell, Jr. |
| 3,906,626 | A | 9/1975 | Riuli |
| 4,139,011 | A | 2/1979 | Benoit et al. |
| 4,373,526 | A | 2/1983 | Kling |

(Continued)

FOREIGN PATENT DOCUMENTS

| CA | 2 200 502 C | 9/1997 |

(Continued)

OTHER PUBLICATIONS

U.S. District Court—S.D. of Florida, Civil Docket for Case No. 1:07-cv-207020, *Stat Medical Devices, Inc. v. Gluco Perfect, L.L.C.* printed Dec. 10, 2008/Miami, FL).

(Continued)

*Primary Examiner*—Darwin P Erezo
(74) *Attorney, Agent, or Firm*—Malloy & Malloy, P.A.

(57) ABSTRACT

A single use lancet device having a housing, a lancet with a piercing tip movably disposed in the housing and structured to move between a cocked orientation and a piercing orientation, and a driving assembly structured to move the lancet into the piercing orientation. A retention member and an engagement hub are further provided and structured to be cooperatively engaged with one another upon the lancet being disposed in the cocked orientation so as to maintain the lancet in the cocked orientation until released by an actuation assembly. Specifically, the actuation assembly is structured to move between an actuated and an un-actuated orientation, movement into the actuated orientation releasing the retention member and the engagement hub from their cooperative engagement with one another and thereby result in movement of the lancet into the piercing orientation. The device also includes a restrictor assembly structured to substantially prevent the actuation assembly from moving out of the actuated orientation, thereby preventing re-firing of the lancet utilizing the actuation assembly.

8 Claims, 4 Drawing Sheets

U.S. PATENT DOCUMENTS

| | | |
|---|---|---|
| 4,414,975 A | 11/1983 | Ryder et al. |
| 4,445,896 A | 5/1984 | Gianturco |
| 4,449,529 A | 5/1984 | Burns et al. |
| 4,469,110 A | 9/1984 | Slama |
| 4,517,978 A | 5/1985 | Levin et al. |
| 4,535,769 A | 8/1985 | Burns |
| 4,539,988 A | 9/1985 | Shirley et al. |
| 4,553,541 A | 11/1985 | Burns |
| 4,573,976 A | 3/1986 | Sampson et al. |
| 4,610,620 A | 9/1986 | Gray |
| 4,628,929 A | 12/1986 | Intengan et al. |
| 4,655,750 A | 4/1987 | Vaillancourt |
| 4,665,959 A | 5/1987 | Takagi |
| 4,715,374 A | 12/1987 | Maggio |
| 4,735,202 A | 4/1988 | Williams |
| 4,735,203 A | 4/1988 | Ryder et al. |
| 4,752,290 A | 6/1988 | Schramm |
| 4,758,231 A | 7/1988 | Haber et al. |
| 4,794,926 A | 1/1989 | Munsch et al. |
| 4,817,603 A | 4/1989 | Turner et al. |
| 4,823,806 A | 4/1989 | Bajada |
| 4,841,985 A | 6/1989 | Wanamaker |
| 4,863,436 A | 9/1989 | Glick |
| 4,869,249 A | 9/1989 | Crossman et al. |
| 4,889,117 A | 12/1989 | Stevens |
| 4,892,097 A | 1/1990 | Ranalletta et al. |
| 4,895,147 A | 1/1990 | Bodicky et al. |
| 4,897,083 A | 1/1990 | Martell |
| 4,907,600 A | 3/1990 | Spencer |
| 4,908,023 A | 3/1990 | Yuen |
| 4,944,736 A | 7/1990 | Holtz |
| 4,969,883 A | 11/1990 | Gilbert et al. |
| 4,983,178 A | 1/1991 | Schnell |
| 4,983,381 A | 1/1991 | Torres Zaragoza |
| 4,990,154 A | 2/1991 | Brown et al. |
| 4,994,045 A | 2/1991 | Ranford |
| 4,994,068 A | 2/1991 | Hufnagle |
| 5,024,660 A | 6/1991 | McNaughton |
| 5,026,388 A | 6/1991 | Ingalz |
| 5,054,499 A | 10/1991 | Swierczek |
| 5,057,079 A | 10/1991 | Tiemann et al. |
| 5,070,885 A | 12/1991 | Bonaldo |
| 5,074,872 A | 12/1991 | Brown et al. |
| 5,086,780 A | 2/1992 | Schmitt |
| 5,088,996 A | 2/1992 | Kopfer et al. |
| 5,116,351 A | 5/1992 | Frassetti |
| 5,125,921 A | 6/1992 | Duschek |
| 5,133,730 A | 7/1992 | Biro et al. |
| 5,147,326 A | 9/1992 | Talonn et al. |
| 5,147,375 A | 9/1992 | Sullivan et al. |
| 5,160,326 A | 11/1992 | Talonn et al. |
| 5,181,609 A | 1/1993 | Spielmann et al. |
| 5,188,620 A | 2/1993 | Jepson et al. |
| 5,201,716 A | 4/1993 | Richard |
| 5,207,696 A | 5/1993 | Matwijcow |
| 5,207,699 A | 5/1993 | Coe |
| 5,212,879 A | 5/1993 | Biro et al. |
| 5,219,333 A | 6/1993 | Sagstetter et al. |
| 5,222,945 A | 6/1993 | Basnight |
| 5,224,950 A | 7/1993 | Prywes |
| 5,230,707 A | 7/1993 | Laderoute |
| 5,241,969 A | 9/1993 | Carson et al. |
| 5,247,972 A | 9/1993 | Tetreault |
| 5,250,026 A | 10/1993 | Ehrlich et al. |
| 5,250,063 A | 10/1993 | Abidin et al. |
| 5,269,799 A | 12/1993 | Daniel |
| 5,269,800 A | 12/1993 | Davis, Jr. |
| 5,279,581 A | 1/1994 | Firth et al. |
| 5,297,599 A | 3/1994 | Bucheli |
| 5,304,136 A | 4/1994 | Erskine et al. |
| 5,304,192 A | 4/1994 | Crouse |
| 5,304,193 A * | 4/1994 | Zhadanov ............ 606/182 |
| 5,312,347 A | 5/1994 | Osborne et al. |
| 5,312,354 A | 5/1994 | Allen et al. |
| 5,312,365 A | 5/1994 | Firth et al. |
| 5,314,441 A | 5/1994 | Cusack et al. |
| 5,318,581 A | 6/1994 | Sunmo |
| 5,318,583 A | 6/1994 | Rabenau et al. |
| 5,318,584 A | 6/1994 | Lange et al. |
| 5,324,303 A | 6/1994 | Strong et al. |
| 5,330,492 A | 7/1994 | Haugen |
| 5,336,199 A | 8/1994 | Castillo et al. |
| 5,346,480 A | 9/1994 | Hess et al. |
| 5,350,392 A | 9/1994 | Purcell et al. |
| 5,356,406 A | 10/1994 | Schraga |
| 5,356,420 A | 10/1994 | Czernecki et al. |
| 5,361,902 A | 11/1994 | Abidin et al. |
| 5,366,470 A | 11/1994 | Ramel |
| 5,395,388 A | 3/1995 | Schraga |
| 5,402,798 A | 4/1995 | Swierczek et al. |
| 5,417,662 A | 5/1995 | Hjertman et al. |
| 5,423,847 A | 6/1995 | Strong et al. |
| 5,439,473 A | 8/1995 | Jorgensen |
| 5,454,828 A | 10/1995 | Schraga |
| 5,462,535 A | 10/1995 | Bonnichsen et al. |
| 5,464,418 A | 11/1995 | Schraga |
| 5,468,233 A | 11/1995 | Schraga |
| 5,469,964 A | 11/1995 | Bailey |
| 5,476,474 A | 12/1995 | Davis et al. |
| 5,487,748 A | 1/1996 | Marshall et al. |
| 5,496,340 A | 3/1996 | Abidin et al. |
| 5,501,672 A | 3/1996 | Firth et al. |
| 5,514,152 A | 5/1996 | Smith |
| 5,518,004 A | 5/1996 | Schraga |
| 5,527,334 A | 6/1996 | Kanner et al. |
| 5,531,713 A | 7/1996 | Mastronardi et al. |
| D376,203 S | 12/1996 | Schraga |
| 5,584,846 A | 12/1996 | Mawhirt et al. |
| 5,599,323 A | 2/1997 | Bonnichsen et al. |
| 5,628,764 A | 5/1997 | Schraga |
| 5,628,765 A | 5/1997 | Morita |
| 5,643,306 A | 7/1997 | Schraga |
| 5,697,916 A | 12/1997 | Schraga |
| 5,706,942 A | 1/1998 | Vila et al. |
| 5,707,384 A | 1/1998 | Kim |
| 5,709,700 A * | 1/1998 | Hirota ............ 606/188 |
| 5,730,753 A | 3/1998 | Morita |
| 5,735,823 A | 4/1998 | Berger |
| 5,738,665 A | 4/1998 | Caizza et al. |
| 5,741,288 A | 4/1998 | Rife |
| 5,746,761 A | 5/1998 | Turchin |
| 5,755,733 A | 5/1998 | Morita |
| 5,772,636 A | 6/1998 | Brimhall et al. |
| 5,792,122 A | 8/1998 | Brimhall et al. |
| 5,797,940 A | 8/1998 | Mawhirt et al. |
| 5,797,942 A | 8/1998 | Schraga |
| 5,836,920 A | 11/1998 | Robertson |
| 5,868,771 A | 2/1999 | Herbert et al. |
| 5,871,494 A | 2/1999 | Simons et al. |
| 5,873,856 A | 2/1999 | Hjertman et al. |
| 5,891,103 A | 4/1999 | Burns |
| 5,908,434 A | 6/1999 | Schraga |
| 5,947,934 A | 9/1999 | Hansen et al. |
| 5,951,530 A | 9/1999 | Steengaard et al. |
| 5,951,582 A | 9/1999 | Thorne et al. |
| 5,954,738 A | 9/1999 | LeVaughn et al. |
| 5,968,021 A | 10/1999 | Ejlersen |
| 5,971,966 A | 10/1999 | Lav |
| 5,980,491 A | 11/1999 | Hansen |
| 5,984,906 A | 11/1999 | Bonnichsen et al. |
| 6,015,397 A | 1/2000 | Elson et al. |
| 6,022,366 A | 2/2000 | Schraga |
| 6,050,977 A | 4/2000 | Adams |
| 6,056,765 A | 5/2000 | Bajaj et al. |

| | | | |
|---|---|---|---|
| 6,074,372 | A | 6/2000 | Hansen |
| 6,077,253 | A | 6/2000 | Cosme |
| 6,106,537 | A | 8/2000 | Crossman et al. |
| 6,110,149 | A | 8/2000 | Klitgaard et al. |
| 6,149,608 | A | 11/2000 | Marshall et al. |
| 6,156,051 | A | 12/2000 | Schraga |
| 6,168,606 | B1 | 1/2001 | Levin et al. |
| 6,190,398 | B1 | 2/2001 | Schraga |
| 6,213,977 | B1 | 4/2001 | Hjertman et al. |
| 6,216,868 | B1 | 4/2001 | Rastegar et al. |
| 6,228,100 | B1 | 5/2001 | Schraga |
| 6,248,120 | B1 | 6/2001 | Wyszogrodzki |
| 6,258,112 | B1 | 7/2001 | Schraga |
| 6,299,626 | B1 | 10/2001 | Viranyi |
| 6,302,869 | B1 | 10/2001 | Klitgaard |
| 6,322,574 | B1 | 11/2001 | Lloyd et al. |
| 6,322,575 | B1 | 11/2001 | Schraga |
| 6,346,114 | B1 | 2/2002 | Schraga |
| 6,358,265 | B1 | 3/2002 | Thorne, Jr. et al. |
| 6,432,120 | B1 | 8/2002 | Teo |
| 6,514,270 | B1 | 2/2003 | Schraga |
| 6,530,937 | B1 | 3/2003 | Schraga |
| 6,719,771 | B1 | 4/2004 | Crossman |
| 6,764,496 | B2 | 7/2004 | Schraga |
| 6,887,253 | B2 | 5/2005 | Schraga |
| 6,918,918 | B1 | 7/2005 | Schraga |
| 6,949,111 | B2 | 9/2005 | Schraga |
| 6,958,072 | B2 * | 10/2005 | Schraga ............... 606/182 |
| 2002/0004649 | A1 | 1/2002 | Jansen et al. |
| 2004/0102802 | A1 | 5/2004 | Marshall |
| 2004/0147948 | A1 | 7/2004 | Schraga |
| 2005/0288699 | A1 | 12/2005 | Schraga |
| 2006/0058828 | A1 | 3/2006 | Shi |
| 2006/0079920 | A1 | 4/2006 | Schraga |
| 2006/0178686 | A1 | 8/2006 | Schraga |

FOREIGN PATENT DOCUMENTS

| | | |
|---|---|---|
| CN | 1411358 A | 4/2003 |
| CN | 2619583 Y | 4/2003 |
| CN | 2621601 Y | 6/2004 |
| CN | ZL 02815771.0 | 10/2004 |
| CN | ZL 00817325.7 | 6/2005 |
| CN | 1846612 A | 10/2006 |
| DE | 203 13 528 U1 | 1/2004 |
| EP | 0 081 665 A1 | 6/1983 |
| EP | 0 115 388 A1 | 8/1984 |
| EP | 0 293 092 A2 | 11/1988 |
| EP | 0 595 148 A1 | 5/1994 |
| EP | 0 633 004 A1 | 1/1995 |
| EP | 0 668 049 A1 | 8/1995 |
| EP | 0 796 592 A2 | 9/1997 |
| EP | 0 894 471 A2 | 2/1999 |
| EP | 0 958 783 A1 | 11/1999 |
| EP | 1 233 706 A1 | 8/2002 |
| EP | 0 940 121 B1 | 6/2005 |
| EP | 1 688 087 A1 | 8/2006 |
| FR | 1.126.718 | 11/1956 |
| GB | 2 052 992 A | 2/1981 |
| HK | 1055234 B | 2/2006 |
| JP | 2000-513624 | 10/2000 |
| JP | 2003-512883 A | 4/2003 |
| JP | 2005-511191 A | 4/2005 |
| JP | 2003-218301 A | 8/2006 |
| MX | 197391 | 3/1996 |
| WO | WO 91/00215 | 1/1991 |
| WO | WO 95/16400 A1 | 6/1995 |
| WO | WO 98/55034 | 12/1998 |
| WO | WO 00/78203 A2 | 12/2000 |
| WO | WO 00/78214 A1 | 12/2000 |
| WO | WO 01/32086 A1 | 5/2001 |
| WO | WO 03/049624 A1 | 6/2003 |
| WO | WO 03/092512 A1 | 11/2003 |

OTHER PUBLICATIONS

Complaint [Case No. 1:07-cv-20720 / Entered Mar. 20, 2007/Miami, FL].
Answer and Affirmitative Defenses of Gluco Perfect, L.L.C. [Case No. 1:07-cv-20720 / Entered Aug. 3, 2007/Miami, FL].
Plaintiff's Reply to Defendant's Affirmative Defenses [Case No. 1:07-cv-20720 / Entered Aug. 27, 2007/Miami, FL].
Gluco Perfect's Motion for Summary Judgement of Non-Infringement [Case No. 1:07-cv-20720 / Entered Oct. 24, 2007/Miami, FL].
Gluco Perfect's Statement of Material Facts in Support of Motion for Summary Judgement of Non-Infringement [Case No. 1:07-cv-20720 / Entered Oct. 25, 2007/Miami, FL].
Gluco Perfect's Memorandum of Law in Support of Its Motion for Summary Judgement of Non-Infringement [Case No. 1:07-cv-20720 / Entered Oct. 24, 2007/Miami, FL].
Affidavit of Kevin R. Mernone in Support of Gluco Perfect's Motion for Summary Judgement [Case No. 1:07-cv-20720 / Entered Oct. 24, 2007/Miami, FL].
Affidavit of Alan H. Pollack in Support of Gluco Perfect's Motion for Summary Judgement of Non-Infringement [Case No. 1:07-cv-20720 / Entered Oct. 24, 2007/Miami, FL].
Gluco Perfect's Request for Oral Argument Concerning Its Motion for Summary Judgement of Non-Infringement [Case No. 1:07-cv-20720 / Entered Oct. 24, 2007/Miami, FL].
Plantiff's Memorandum of Law in Support of Its Opposition to Defendant's Motion for Summary Judgement . . . [Case No. 1:07-cv-20720 / Entered Nov. 19, 2007/Miami, FL].
Plantiff's Statement of Material Facts in Support of Its Opposition to Defendant's Motion for Summary Judgement [Case No. 1:07-cv-20720 / Entered Nov. 19, 2007/Miami, FL].
Notice of Filng [Case No. 1:07-cv-20720 / Entered Nov. 19, 2007/Miami, FL].
Gluco Perfect's Reply Memorandum of Law in Support of Its Motion for Summary Judgement of Non-Infringement [Case No. 1:07-cv-20720 / Entered Dec. 11, 2007/Miami, FL].
Reply Affidavit of Alan H. Pollack in Support of Gluco Perfect's Motion for Summary Judgement of Non-Infringement [Case No. 1:07-cv-20720 / Entered Dec. 11, 2007/Miami, FL].
Gluco Perfect's Motion to Stay Discovery or in the Alternative for a Protective Order [Case No. 1:07-cv-20720 / Entered Jan. 9, 2008/Miami, FL].
Affidavit of Alan H. Pollack in Support of Gluco Perfect's Motion to Stay Discovery or a Protective Order [Case No. 1:07-cv-20720 / Entered Jan. 9, 2008/Miami, FL].
Plantiff's Motion to Strike Defendant's Reply Memorandum and Reply Affidavit, or, in the Alternative, Leave to File . . . [Case No. 1:07-cv-20720/Entered Jan. 14, 2008/Miami, FL].
Gluco Perfect's Memorandum in Opposition to Stat's Motion to Strike Gluco Perfect's Summary Judgement Reply [Case No. 1:07-cv-20720 / Entered Jan. 22, 2008/Miami, FL].
Affidavit of Alan H. Pollack in Opposition to Stat's Motion to Strike Gluco Perfect's Summary Judgement Reply [Case No. 1:07-cv-20720 / Entered Jan. 22, 2008/Miami, FL].
Plaintiff's Memorandum of Law in Support of Its Opposition to Defendant's Motion to Stay Discovery or for a . . . [Case No. 1:07-cv-20720 / Entered Jan. 28, 2008/Miami, FL].
Plantiff's Reply Memorandum of Law in Support of Its Motion to Strike [Case NO. 1:07-cv-20720 / Entered Feb. 1, 2008/Miami, FL].
Gluco Perfect's Reply in Support of Its Motion to Stay Discovery or in the Alternative for a Protective Order [Case No. 1:07-cv-20720 / Entered Feb. 7, 2008/Miami, FL].
Affidavit of Alan H. Pollack in Support of Gluco Perfect's Motion to Stay Discovery [Case No. 1:07-cv-20720 / Entered Feb. 7, 2008/Miami, FL].
Affidavit of Kevin R. Mernone in Support of Gluco Perfect's Motion to Stay Discovery [Case No. 1:07-cv-20720 / Entered Feb. 7, 2008/Miami, FL].
Supplement to Gluco Perfect's Reply in Support of Its Motion to Stay Discovery or in the Alternative for a . . . [Case No. 1:07-cv-20720 / Entered Feb. 19, 2008/Miami, FL].

Transcript of Oral Argument [Case No. 1:07-cv-20720 / Entered Mar. 28, 2008/Miami, FL].
Order Denying Defendant's Motion for Summary Judgement [Case No. 1:07-cv-20720 / Entered Apr. 10, 2008/Miami, FL].
Gluco Perfect's Motion to Compel Stat to Answer Completely Interrogatories 1-6, 8, 10 and 12-17 and Presentation . . . [Case No. 1:07-cv-20720 / Entered Jul. 30, 2008/Miami, FL].
Gluco Perfect's Motion to Compel Stat to Produce Material Concerning Document Requests 1-4, 10, 11, 26-28, 51, 52 . . . [Case No. 1:07-cv-30720 / Entered Jul. 30, 2008/Miami, FL].
Gluco Perfect's Motion to Determine the Sufficiecy of Stat's Objections—to Gluco Perfect's Requests for Admission . . . [Case No. 1:07-cv-20720/Entered Jul. 30, 2008/Miami, FL].
Affidavit of Alan H. Pollack in Support of Gluco Perfect's Motions to Compel Discovery [Case No. 1:07-cv-20720 / Entered Jul. 30, 2008/Miami, FL].
Gluco Perfect's Consolidated Reply in Support of its Motions to Compel Discovery From Stat [Case No. 1:07-cv-20720 / Entered Sep. 25, 2008/Miami, FL].
Gluco Perfect Reply Appendix Concerning its Motions to Compel Discovery [Case No. 1:07-cv-20720 / Entered Sep. 25, 2008/Miami, FL].
Gluco Perfect's Motion for Summary Judgement of Non-Infringement [Case No. 1:07-cv-20720 / Entered Dec. 5, 2008/Miami, FL].
Gluco Perfect's Memorandum of Law in Support of its Motion for Summary Judgement of Non-Infringement [Case No. 1:07-cv-20720 / Entered Dec. 5, 2008/Miami, FL].
Gluco Perfect's Statement of Material Facts in Support of its Motion for Summary Judgement of Non-Infringement [Case No. 1:07-cv-20720 / Entered Dec. 5, 2008/Miami, FL].
Declaration of Kevin R. Mernone in Support of Gluco Perfect's Motion for Summary Judgement [Case No. 1:07-cv-20720 / Entered Dec. 5, 2008/Miami, FL].
Declaration of Henry E. Bonsecour in Support of Gluco Perfect's Motion for Summary Judgement [Case No. 1:07-cv-20720 / Entered Dec. 5, 2008/Miami, FL].
Declaration of Ronald H. Smith in Support of Gluco Perfect's Second Motion for Summary Judgement of Non-Infringment [Case No. 1:07-cv-20720 / Entered Dec. 5, 2008/Miami, FL].
Declaration of H. Howard Wang in Support of Gluco Perfect's Motion for Summary Judgement of Non-Infringment [Case No. 1:07-cv-20720 / Entered Dec. 5, 2008/Miami, FL].
U.S. District Court—S.D. of Florida, Civil Docket for Case No. 1:02-cv-23210, *Abulhaj, et al v. Schraga*, et al. (Printed Dec. 10, 2008/Miami, FL).
Complaint for Declaratory Judgement [Case No. 1:02-cv-23210 / Entered Nov. 1, 2002/Miami, FL].
Answer, Affirmative Defenses and Counterclaims [Case No. 1:02-cv-23210 / Entered Dec. 9, 2002/Miami, FL].
Motion to Dismiss Counts I and III of Complaint [Case No. 1:02-cv-23210 / Entered Dec. 9, 2002/Miami, FL].
Plaintiffs' Response to Motion to Dismiss Counts I and III of Plaintiffs' Complaint [Case No. 1:02-cv-23210 / Entered Dec. 27, 2002/Miami, FL].
Plaintiffs' Response to Motion to Dismiss Counts I and III of Plaintiffs' Complaint [Case No. 1:02-cv-23210 / Entered Dec. 30, 2002/Miami, FL].
Plaintiffs' Response to Counterclaim for Patent Infringement [Case No. 1:02-cv-23210 / Entered Jan. 2, 2003/Miami, FL].
Reply to Response to Motion to Dismiss Counts I and III of Complaint [Case No. 1:02-cv-23210 / Entered Jan. 3, 2003/Miami, FL].
Motion to Continue Trial and Pre-Trail Deadlines [Case No. 1:02-cv-23210 / Entered Jan. 21, 2003/Miami, FL].
Declaration of Andrew W. Ransom in Support of Motion for Continuance [Case No. 1:02-cv-23210 / Entered Jan. 21, 2003/Miami, FL].
Plaintiffs' Initial Disclosures Pursuant to Fed.R.Civ.P.26(a)(3); and Local Rule 16(1)(d) [Case No. 1:02-cv-23210 / Entered Jan. 30, 2003/Miami, FL].
Plaintiffs' Combined Motion and Memorandum of Fact and Law to Bifurcate Trial and Limit Discovery [Case No. 1:02-cv-23210 / Entered Feb. 14, 2003/Miami, FL].

Defendants' Memorandum in Opposition to Plaintiffs' Combined Motion and Memorandum to Bifurcate Trial and Limit . . . [Case No. 1:02-cv-23210 / Entered Feb. 28, 2003/Miami, FL].
Defendant Stat Medical Devices, Inc.'s Motion to Compel [Case No. 1:02-cv-23210 / Entered Mar. 18, 2003/Miami, FL].
Defendant Schraga's Motion to Compel Complete Responses to Defendant Schraga's First Set of Interrogatories to . . . [Case No. 1:02-cv-23210 / Entered Mar. 18, 2003/Miami, FL].
Defendant Stat Medical Devices, Inc.'s Motion to Strike Plaintiffs' Pleadings, Impose Sanctions and Compel . . . [Case No. 1:02-cv-23210 / Entered Mar. 28, 2003/Miami, FL].
Plaintiffs' Memorandum of Fact and Law in Support of Plaintiffs' Motion to Compel Production of Documents [Case No. 1:02-cv-23210 / Entered Apr. 3, 2003/Miami, FL].
Amended Complaint for Declaratory Judgement [Case No. 1:02-cv-23210 / Entered Apr. 7, 2003/Miami, FL].
Plaintiffs' Response to Stat Medical Devices Motion to Compel [Case No. 1:02-cv-23210 / Entered Apr. 7, 2003/Miami, FL].
Plaintiffs' Motion to Amend Complaint [Case No. 1:02-cv-23210 / Entered Apr. 7, 2003/Miami, FL].
Plaintiffs' Response to Schraga's Motion to Compel Responses to Schraga's First Set of Interrogatories [Case No. 1:02-cv-23210 / Entered Apr. 7, 2003/Miami, FL].
Plaintiff's Memorandum of Fact and Law in Support of Plaintiffs' Motion to File Amended Complaint [Case No. 1:02-cv-23210 / Entered Apr. 7, 2003/Miami, FL].
Defendant Schraga's Reply to Plaintiffs' Response to Motion to Compel [Case No. 1:02-cv-23210 / Entered Apr. 21, 2003/Miami, FL].
Defendant Stat Medical Devices, Inc.'s Reply to Plaintiffs' Response to Motion to Compel [Case No. 1:02-cv-23210 / Entered Apr. 21, 2003/Miami, FL].
Defendants' Response to Motion to Compel and Cross-Motion for Protective Order [Case No. 1:02-cv-23210 / Entered Apr. 21, 2003/Miami, FL].
Defendants Response to Motion to File Amended Complaint [Case no. 1:02-cv-23210 / Entered Apr. 24, 2003/Miami, FL].
Answer and Affirmative Defenses to Amended Complaint [Case No. 1:02-cv-23210 / Entered May 8, 2003/Miami, FL].
Plaintiffs' Answer to Defendants' Counterclaim for Patent Infringement and Affirmative Defenses [Case No. 1:02-cv-23210 / Entered May 16, 2003/Miami, FL].
Defendants' Response to Plaintiffs' Motion to Amend Complaint [Case No. 1:02-cv-23210 / Entered Jun. 3, 2003/Miami, FL].
Plaintiffs' Reply to Defendants' Response to Plaintiffs' Motion to Amend Complaint [Case No. 1:02-cv-23210 / Entered Jun. 13, 2003/Miami, FL].
Response to Cross-Motion to Compel Compliance with Subpoenas Duces Tecum [Case No. 1:02-cv-23210 / Entered Jun. 19, 2003/Miami, FL].
Defendants' Unopposed Motion to File Document Under Seal [Case No. 1:02-cv-23210 / Entered Jul. 9, 2003/Miami, FL].
Order Granting Plaintiffs' Motion to Amend Complaint and Revised Scheduling Order [Case No. 1:02-cv-23210 / Entered Jul. 10, 2003/Miami, FL].
Second Amended Complaint for Declaratory Judgement [Case No. 1:02-cv-23210 / Entered Jul. 10, 2003/Miami, FL].
Defendants' Emergency Motion to Compel Plaintiffs to Produce Shi for Deposition or be Excluded from Presenting him . . . [Case No. 1:02-cv-23210 / Entered Jul. 10, 2003/Miami, FL].
Defendants' Motion to Dismiss Count III of Plaintiffs' Second Amended Complaint [Case No. 1:02-cv-23210 / Entered Jul. 30, 2003/Miami, FL].
Answer, Affirmative Defenses and Counterclaims to Second Amended Complaint [Case No. 1:02-cv-23210 / Entered Jul. 30, 2003/Miami, FL].
Defendants' Reply to Response to Emergency Motion to Compel Plaintiffs to Produce Shi for Deposition or be Excluded . . . [Case No. 1:02-cv-23210 / Entered Aug. 5, 2003/Miami, FL].
Plaintiffs' Answer and Affirmative Defenses to Defendant's Counterclaim [Case No. 1:02-cv-23210 / Entered Aug. 19, 2003/Miami, FL].

Defendants' Reply to Plaintiffs' Response Motion to Dismiss Count III of Plaintiffs' Second Amended Complaint [Case No. 1:02-cv-23210 / Entered Aug. 26, 2003/Miami, FL].

Defendants' Response to Plaintiffs' Motion to Compel and Cross Motion for Protective Order [Case No. 1:02-cv-23210 / Entered Oct. 20, 2003/Miami, FL].

Defendants' Response to Plaintiffs' Emergency Motion to Stay and Unopposed Cross-Motion for Temporary Stay of Action [Case No. 1:02-cv-23210 / Entered Oct. 21, 2003/Miami, FL].

Order Staying Proceeding and Administratively Closing Case [Case No. 1:02-cv-23210 / Entered Oct. 30, 2003/Miami, FL].

Order Granting Defendants' Motion to Dismiss Count III of the Second Amended Complaint and Denying Plaintiffs' . . . [Case No. 1:02-cv-23210 / Entered Jan. 12, 2004/Miami, FL].

Plaintiffs' Combined Emergency Motion to Stay Proceedings Subject to the Outcome of Reexamination Proceedings . . . [Case No. 1:02-cv-23210 / Entered Jan. 20, 2004/Miami, FL].

Defendants' Motion for Protective Order Seeking Ruling as a Scope of Waiver of Attorney-Client Privilege [Case No. 1:02-cv-23210 / Entered Jan. 26, 2004/Miami, FL].

Defendants' Renewed Motion to Compel Plaintiffs to Answer and/or Supplement Discovery [Case No. 1:02-cv-23210 / Entered Jan. 26, 2004/Miami, FL].

Defendants'/Counterplaintiffs' Motion for Acceptance of Proposed Claim Construction of United States Patent . . . [Case No. 1:02-cv-23210 / Entered Jan. 26, 2004/Miami, FL].

Defendants/Counterplaintiffs' Motion for Summary Judgement [Case No. 1:02-cv-23210 / Entered Jan. 26, 2004/Miami, FL].

Plaintiffs' Combined Motion to Compel and Motion for Hearing [Case No. 1:02-cv-23210 / Entered Jan. 26, 2004/Miami, FL].

Defendants/Counterplaintiffs' Statement of Facts as to Which There is no Genuine Issue to be Tried [Case No. 1:02-cv-23210 / Entered Jan. 26, 2004/Miami, FL].

Defendants/Counterplaintiffs' Response to 'Plaintiffs' Combined Emergency Motion to Stay Proceedings Subject to . . . [Case No. 1:02-cv-23210 / Entered Jan. 30, 2004/Miami, FL].

Plaintiffs' Combined Unopposed Motion to Stay Plaintiffs' Deadline for Response to Defendants' Outstanding Motions . . . [Case No. 1:02-cv-23210 / Entered Feb. 2, 2004/Miami, FL].

Defendants' Response to Motion to Strike Expert Reports [Case No. 1:02-cv-23210 / Entered Feb. 4, 2004/Miami, FL].

Plaintiffs' Reply in Further Support of Plaintiffs' Combined Motion to Stay Proceedings Subject to the Outcome of . . . [Case No. 1:02-cv-23210 / Entered Feb. 6, 2004/Miami, FL].

Defendants' Response to Plaintiffs' Combined Motion to Compel and Motion for Hearing [Case No. 1:02-cv-23210 / Entered Feb. 8, 2004/Miami, FL].

Plaintiffs' Response to Defendants' Motion for Protective Order Seeking Ruling as to Scope of Waiver of Attorney . . . [Case No. 1:02-cv-23210 / Entered Feb. 17, 2004/Miami, FL].

Plaintiffs' /Counterdefendants' Response to Defendants'/Counterplaintiffs' Motion for Acceptance of Proposed Claim . . . [Case No. 1:02-cv-23210 / Entered Feb. 17, 2004/Miami, FL].

Defendants' Reply to Response to Motion for Acceptance of Claim Construction/Request for Hearing [Case No. 1:02-cv-23210 / Entered Feb. 25, 2004/Miami, FL].

Defendants' Reply to Plaintiffs' Response to Defendants' Motion for Summary Judgement [Case No. 1:02-cv-23210 / Entered Feb. 25, 2004/Miami, FL].

Notice of Filing Assignment of Patent Rights [Case No. 1:02-cv-23210 / Entered Feb. 26, 2004/Miami, FL].

Notice of Filing Rebuttal Expert Report [Case No. 1:02-cv-23210 / Entered Feb. 26, 2004/Miami, FL].

Notice of Filing Corrected Document [Case No. 1:02-cv-23210 / Entered Feb. 27, 2004/Miami, FL].

Defendants' Notice of Settlement and Unopposed Request for Continuance to Submit Settlement Agreement to Bankruptcy . . . [Case No. 1:02-cv-23210 / Entered Mar. 5, 2004/Miami, FL].

Stipulation of Dismissal [Case No. 1:02-cv-23210 / Entered Jun. 7, 2004/Miami, FL].

* cited by examiner

SINGLE USE LANCET DEVICE

CLAIM OF PRIORITY

The present application is a continuation patent application of previously filed application having Ser. No. 10/171,464, which was filed on Jun. 13, 2002, and which has now matured into U.S. Pat. No. 6,958,072, which is also a continuation patent application of previously filed patent application having Ser. No. 09/709,738, which was filed on Nov. 10, 2000 and has now matured into U.S. Pat. No. 6,514,270, which claims priority to provisional patent application now abandoned having Ser. No. 60/297,826 and a filing date of Jun. 13, 2001.

BACKGROUND OF THE INVENTION

1. Field of the Invention

The present invention relates to a single use lancet device structured to be conveniently and effectively utilized for various blood sampling procedure, but which is also substantially safe, preventing re-firing of the device after it has been used, and thereby preventing and/or substantially minimizing inadvertent contamination of a patient and/or other personnel as a result of a used and potentially contaminated lancet. Furthermore, the device is compact and easy to utilize in a cost effective and preferably fully disposable manner.

2. Description of the Related Art

Lancets are commonly utilized instruments which are employed both in hospitals and other medical facilities, as well as by private individuals, such as diabetics, in order to prick or pierce a patient's skin, typically on a finger of a patient, thereby leading to the generation of a blood sample which can be collected for testing. Because of the wide spread use of such lancets, there are a variety of lancet devices which are available for utilization by patients and/or practitioners in a variety of different circumstances.

For example, a typical lancet may merely include a housing with a sharp piercing tip that is pushed into the patient's skin. More commonly, however, lancet devices, which house a piercing tip and/or a lancet, have been developed which effectively encase and fire the lancet into the patient's skin, thereby eliminating the need for the person taking the sample to actually push the lancet tip into the skin.

Within the various types of specialized lancet devices, one variety is typically configured for multiple and/or repeated uses, while another category is particularly configured for single use, after which the entire device is disposed of. Looking in particular to the single use, disposable lancet devices, such devices typically include a housing which contains and directs or drives a piercing tip into the patient's skin, and which is disposed of along with the used lancet. Naturally, so to make such disposable devices cost effective for frequent use, such devices tend to be rather simplistic in nature providing only a sufficient mechanism for firing, and not overly complicating the design so as to minimize that cost.

While existing single use devices are generally effective for achieving the piercing of the skin required for effective operation, such single use, disposable devices typically do not incorporate a large number of safety features to ensure the safe use and disposal of the device. For example, one primary area of safety which must be addressed with all lancet devices pertains to the purposeful and/or inadvertent reuse of a contaminated lancet. Unfortunately, most currently available single use lancet devices are configured such that after a use thereof has been achieved, it is possible for a patient to re-cock the device, thereby allowing for a subsequent, inappropriate use.

As a result, it would be highly beneficial to provide a single use lancet device which is substantially compact and disposable, can be manufactured in a substantially cost effective manner, and which nevertheless is substantially safe to utilize, affirmatively preventing re-use, once contaminated. Additionally, it is noted that while other devices may be provided to prevent the lancet from even being cocked, it would still be beneficial to provide a device that, even if the lancet is re-cocked, does not allow for additional and/or secondary firing.

SUMMARY OF THE INVENTION

The present invention is directed to a single use lancet device of the type commonly utilized for various blood sampling purposes. In particular, the single use lancet device of the present invention includes a housing and a lancet. The lancet, which also includes a piercing tip, is movably disposed in the housing and is structured to move at least between a cocked orientation and a piercing orientation. A driving assembly is provided so as to actually move the lancet at least temporarily into the piercing orientation.

The lancet may be retained in the cocked orientation by means of at least one embodiment of a retention assembly. In this embodiment of the present invention, at least one retention member and a corresponding engagement hub are cooperatively disposed. In particular, the engagement hub is structured to be cooperatively engaged with the retention member, at least when the lancet is disposed in the cocked orientation. As a result, the retention member and the engagement hub, which may be cooperatively engaged with the housing and the lancet, effectively maintain the lancet in the cocked orientation until they are released from that engagement with one another. As such, it is seen, in this embodiment, that when the lancet is ready for use, it is maintained in the cocked, ready to fire orientation until that time.

In order to release the lancet, and more particularly the cooperative engagement between the retention member and the engagement hub of the illustrated embodiment, the present invention further includes an actuation assembly. Specifically the actuation assembly is structured to move between an actuated orientation and an un-actuated orientation. In this regard, movement of the actuation assembly into the actuated orientation is structured to release at least the retention member and the engagement hub from their cooperative engagement with one another, thereby resulting in movement of the lancet into the piercing orientation.

In order to substantially minimize the inadvertent re-use of the single use lancet device of the present invention, a restriction assembly is also preferably provided. Specifically, the restriction assembly is structured to substantially prevent the actuation assembly from moving from a piercing orientation towards a cocked or un-actuated orientation and out of the aforementioned actuated orientation. In this regard, the restriction assembly may include a stop member preferably in the form of at least one abutment structure that is fixedly mounted on the housing. In addition, the restriction assembly includes a restrictor member mounted at least on the lancet member and in abutting relation with the stop member as the restrictor member travels in the direction of the cocked or un-actuated orientation from the piercing orientation. As such, once the lancet device of the present invention has been fired the actuation assembly and/or lancet cannot move back into its un-actuated orientation/cocked orientation for a subsequent firing, regardless of whether the lancet itself may or may not be moved back into the cocked orientation.

These and other features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Looking to the Figures, the present invention is directed to a single use lancet device, generally indicated as 10. In particular, the single use lancet device 10 is structured to be utilized so as to pierce a patient's skin, such as with the piercing tip 25 of a lancet 24 in order to obtain a blood specimen from the patient. Furthermore, the present single use lancet device 10 is preferably configured to be substantially small and compact, and structured so as to permit only a single use thereof. The spread of disease and/or other contaminants from the inadvertent and/or deliberate reuse of such a single use lancet device 10 will thereby be prevented.

The single use lancet device 10 of the present invention preferably includes a housing 20. The housing 20 is preferably generally rigid and compact so as to be easily and comfortably held and manipulated by the user. In this regard, the housing 20 may be contoured and/or have any configuration that can be effectively and conveniently held and operated by a user. Movably contained within the housing is a lancet 24. In particular, the lancet 24 preferably includes a piercing tip 25 that extends outwardly from a front or leading end 24' of a movable body 24", which is to be considered a part of the lancet 24. Further, the lancet 24 is structured to be contained within an interior of the housing 20 and to move therein, as will be described in greater detail hereinafter.

Figure 5:
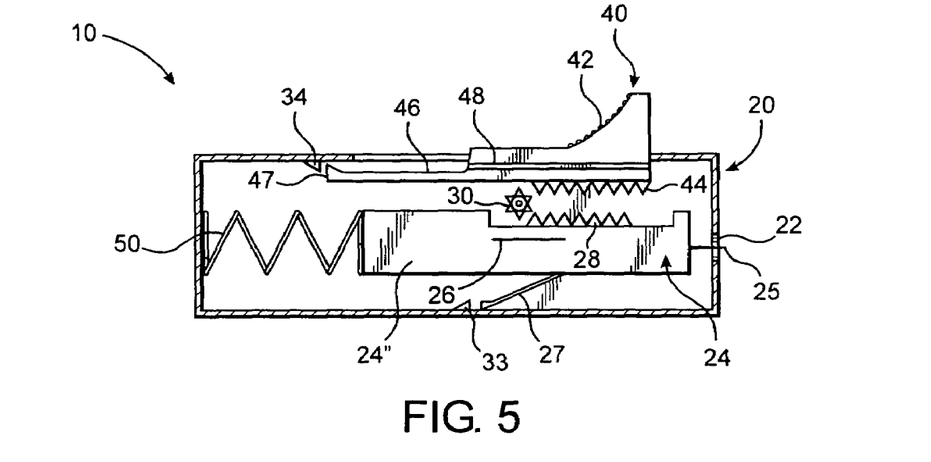
FIG. 5 is a side view of the embodiment of FIG. 2 illustrating the lancet disposed in a piercing orientation and the actuation assembly in a locked orientation.
Figure 6:
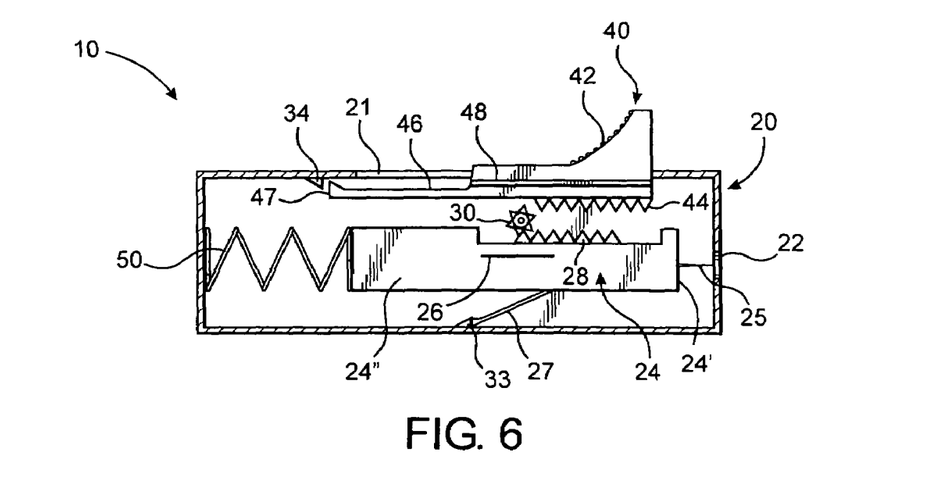
FIG. 6 is a side view of the embodiment of FIG. 2 illustrating a retracted orientation after the firing of the single use lancet device of the present invention.

A driving assembly, preferably in the form of a biasing element 50, is disposed and/or connected relative to the lancet 24 so as to force it into a piercing orientation, best illustrated in FIG. 5. Furthermore, the lancet 24 preferably only temporarily achieves the piercing orientation illustrated in FIG. 5, after which it is retracted into an interior of the housing 20, as illustrated in FIG. 6. Once retracted, the piercing tip 25 is disposed within the housing 20 and is thereby effectively concealed and prevented from inadvertent contact with the user, patient, etc. Moreover, as will also be described hereinafter, in the retracted orientation of FIG. 6, one or more structural components are preferably incorporated in the single use lancet device 10 that prevent the lancet 24 from being effectively re-fired.

Figure 1:
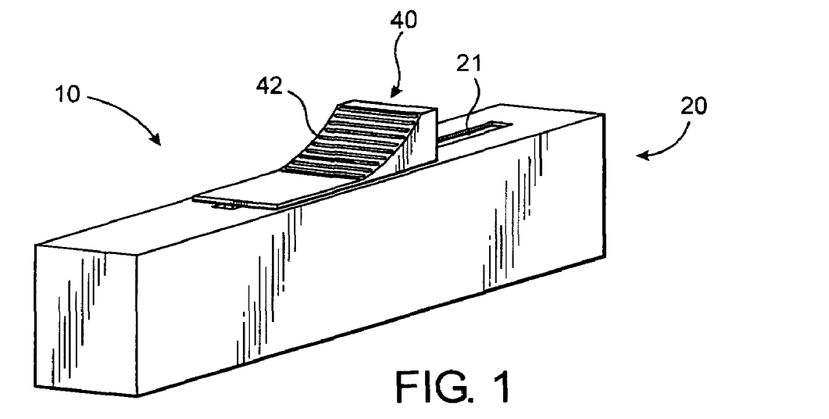
FIG. 1 is a rear perspective illustration of an embodiment of the single use lancet device of the present invention.
Figure 2:
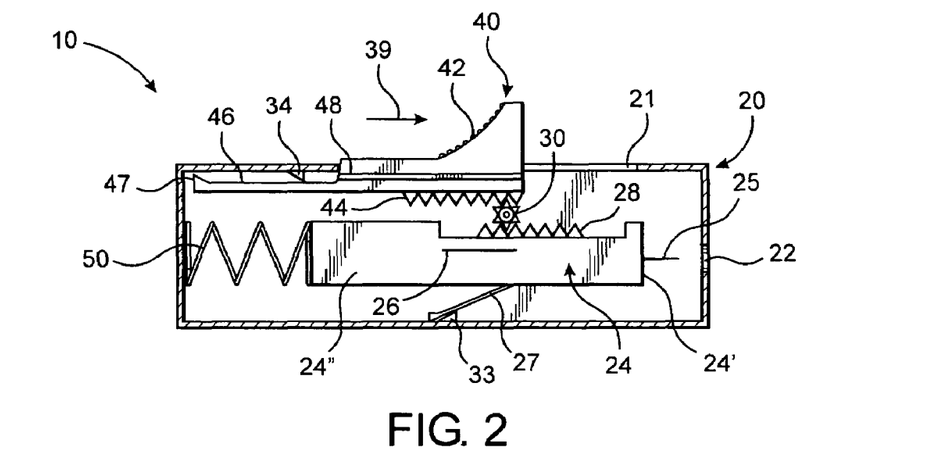
FIG. 2 is an interior longitudinal cross sectional view of an embodiment of the single use lancet device of the present invention in an un-cocked, un-fired orientation.
Figure 3:
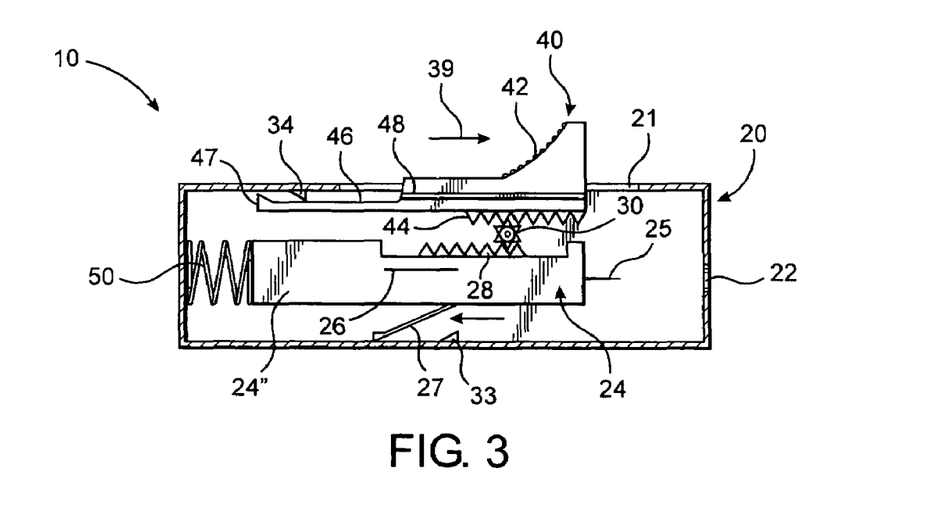
FIG. 3 is an illustration of the embodiment of FIG. 2 wherein the lancet is disposed under tension and in a ready to fire orientation.
Figure 4:
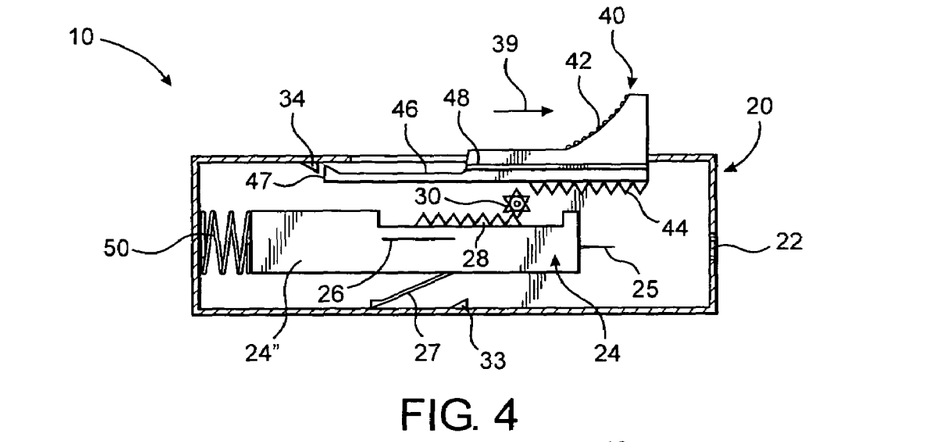
FIG. 4 is side view of the embodiment of FIG. 2 illustrating a release point between the lancet and the actuation assembly so as to permit the lancet to be fired.

In order to achieve movement of the lancet 24 into a generally cocked orientation, where it is under tension, the single use lancet device 10 also preferably includes an actuation assembly 40. In addition, the lancet 24 preferably moves within the housing 20 while being maintained in a properly aligned orientation by one or more guide tracks or wings 26. Further, various embodiments of the present invention include a positioning assembly which comprises at least one positioning member. The positioning member may be in the form of a gear member 30 movably and detachably connected between the actuation assembly 40 and the lancet 24. In particular, the positioning assembly is configured so as to move the lancet 24 rearward, compressing the biasing element 50 and placing the lancet 24 under tension, when the actuation assembly 40 is pushed forward as indicated by directional arrow 39, such as by a thumb of the user. As a result, when an unfired lancet 24, as illustrated in FIG. 2, is grasped, the user merely pushes forward on the actuation assembly 40. The actuation assembly 40 at least partially extends into the interior of the housing 20, such as by passing through an actuation access opening 21. When moved forward, the lancet 24 is caused to move rearward toward or into the cocked orientation by virtue of the at least one positioning member such as gear 30.

Eventually, the actuation assembly 40 will be pushed forward to a sufficient degree to achieve a release point where the positioning member or gear 30 will be released or detached from concurrent inter connection with both the lancet 24 and the actuation assembly 40, as will be described hereinafter. Upon the actuation assembly reaching the release point, the tension exerted on the lancet 24 by the biasing element 50 causes the lancet 24 to be driven forward temporarily into its piercing orientation, as illustrated in FIG. 5. Subsequently, as disclosed in FIG. 6, the biasing element 50 will return automatically to its normally relaxed position, thereby forcing the lancet 24, and in particular the piercing tip 25, back into the housing 20 into a retracted orientation disclosed in FIG. 6. In its retracted orientation, the piercing tip 25 will be contained within the housing 20 thereby preventing inadvertent contact or engagement of the piercing tip 20 with any person or object.

Looking to the embodiment of FIGS. 1 through 6, the actuation assembly 40 includes an exterior portion 42 which is structured to be manipulated by a user, such as by engagement with the user's thumb. As such, the actuation assembly 40 preferably slides relative to the housing 20 in a generally parallel orientation to the movement of the lancet 24, preferably through the provision of a guide track or wing 48.

Exposed, preferably on an underside of the actuation assembly 40, however, is a track element 44.

More specifically, the track element 44 is structured to operatively engage the rotating gear 30 of the positioning assembly. The gear 30 is connected to the housing 20, but freely rotates therein. Moreover, the lancet 24 preferably also includes a corresponding track 28 which also engages the interconnecting, rotating gear 30. Accordingly, as the track 44 on the actuation assembly 40 moves forward, the gear 30 rotates clockwise and because of its engagement with the track 28, causes the lancet 24 to be pulled or moved rearward within the housing 20. The track 44 on the actuation assembly 40, however, has only a predetermined limited length, and as such, when a clearance point is reached, as in FIG. 4, the track 44 no longer engages the gear 30. The gear 30 can then freely rotate allowing the lancet 24 to be urged forward into the piercing orientation as a result of the force exerted thereon by the biasing element 50. In this regard, one fluid, forward pushing movement of the actuation assembly 40 achieves a movement of the lancet 24 first into the cocked orientation and then into the piercing orientation. In the piercing orientation the piercing tip 25 engages a patient as intended.

In order to prevent the single use lancet device 10 of the present invention from being re-used, one or more safety structures have been provided. In particular, a restriction assembly is preferably provided and cooperatively disposed between the lancet 24 and the housing 20. In the embodiment of FIG. 2, the restriction assembly comprises a restrictor member, which may take the form of a biasing element 27 protruding from the movable body 24'' of the lancet 24. When moving in a forward direction (see directional arrow 39), the biasing element 27 is structured to freely pass over a stop member or abutment 33 preferably fixedly disposed on the interior of the housing 20. As the lancet 24 is forced into its piercing orientation, the biasing element 27 does not restrictively engage abutment 33. However, as the lancet 24 is retracted in a rearward direction, back into the interior of the housing 20, the biasing element 27 and the stop member or abutment 33 are relatively disposed and cooperatively structured to restrictively engage one another and limit the rearward movement of the lancet 24. As a result, the lancet 24 can not be pushed rearward into a generally cocked orientation and therefore can not be re-fired.

As an additional safety measure, however, the actuation assembly 40 is preferably configured such that it may fire the single use lancet device 10 only a single time. Looking to the embodiment of FIG. 2, the actuation assembly 40 may include a trailing portion 46 within an abutment head 47. In particular, the abutment head 47 is preferably generally angled, or otherwise configured, to move freely over a corresponding abutment element 34 in the housing 20 when the actuation assembly 40 is moved forward (see directional arrow 39) during firing of the lancet 24. Accordingly, when the actuation assembly 40 has moved forward sufficiently so as to release or be disconnected from the gear 30, the lancet 24 will be forced forward, into the piercing orientation. The abutment head 47 will then have passed over the cooperatively structured stop or abutment element 34. Subsequent to the firing of the lancet 24, restrictive engagement between the abutment element 34 and the abutment head 47 will limit rearward movement of the actuation assembly 40 to a point where it cannot re-engage the gear 30 of the positioning assembly. Re-firing of the single use lancet device 10 is thereby further prevented.

Figure 7:
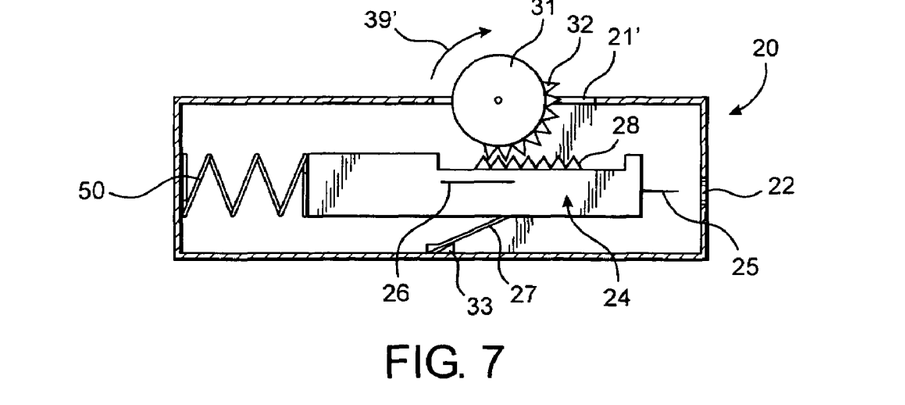
FIG. 7 is a side cross sectional view of an alternative embodiment of the single use lancet device of the present invention.

Looking to the embodiment of FIG. 7, the actuation assembly differs from the embodiment of FIGS. 1 through 6 and comprises a rotationally mounted actuation member 31 that protrudes outwardly from housing 20 through an access opening 21'. In this embodiment, the positioning member of the positioning assembly comprises a gear segment 32 formed along a portion of the periphery of actuation member 31. As such, as the actuation member 31 is rotated by exerting a pushing force thereon, as indicated by directional arrow 39', the lancet 24 is moved rearwardly and placed under tension by the biasing element 50. Eventually, however, the forward rotation of the large central gear at least partially defining the actuation member 31 will be such that the gear segment 32 will be disengaged from the track 28 on the lancet 24. The lancet 24 will thereby be released causing it to be effectively fired and move into its piercing orientation. In such an embodiment, any of a variety of different components could be utilized so as to prevent subsequent movement of the large central gear of the actuation member 31. However, a restriction assembly comprising a restrictor member or biasing element 27 and stop member or abutment element 33, as described above will provide sufficient safety to prevent re-firing of the lancet 24.

Figure 8:
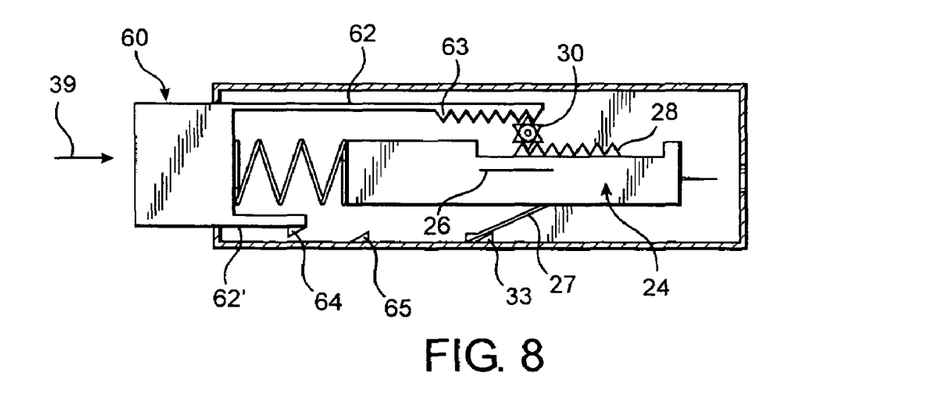
FIG. 8 is a side cross sectional view of yet another alternative embodiment of the single use lancet device of the present invention.

FIG. 8 represents yet another embodiment of the present invention, wherein the actuation assembly may be configured as a rear push button, generally indicated as 60. In this embodiment, the rear push button actuation assembly 60 includes an elongate element 62 mounted on the interior of the housing 20 and provided with a gear track 63 formed thereon. This gear track 63 is disposed and configured to movably engage and manipulate the positioning member or rotating gear 30. The gear 30 is also disposed in movably engaging relation with the gear track 28 fixedly secured to lancet 24. Forward movement of the push button actuation assembly 60 and the track 63, in accordance with directional arrow 39, causes the appropriate rearward movement of the lancet 24 due to the interconnection of the gear 30 with both the tracks 63 and 28. The lancet 24 is thereby compressed against the biasing element 50 of the driving assembly and then subsequently released causing the firing of the lancet 24.

In such an embodiment, the restriction assembly may comprise a restrictor member in the form of an abutment head 64 and a corresponding stop member in the form of an abutment element 65 associated with the elongated element 62 or with an oppositely disposed element 62', as illustrated in FIG. 8. In either such embodiment, after lancet 24 has been fired due to sufficient forward movement of the push button actuation assembly 60 into a compressed position, the push button actuation assembly 60 can not be withdrawn from its compressed position within the housing 20 and it can not be re-used.

Figure 9:
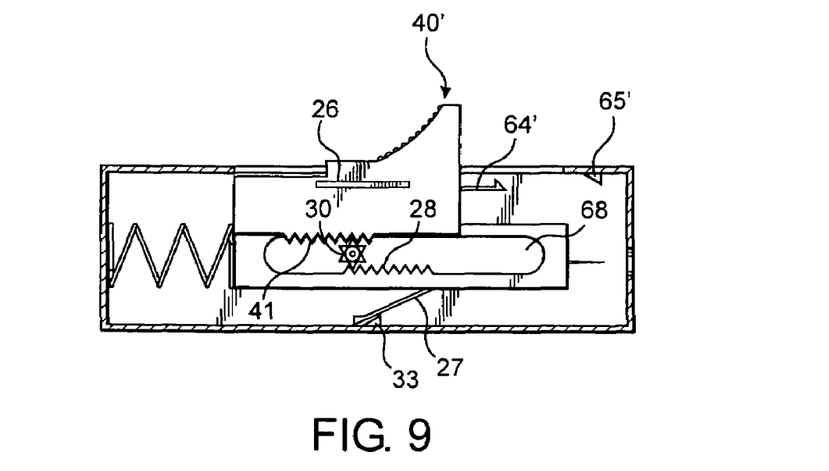
FIG. 9 is a side cross sectional view of still another embodiment of the single use lancet device of the present invention.
Figure 10:
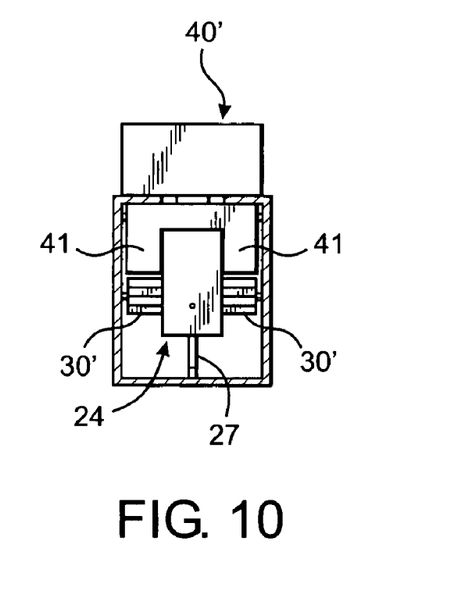
FIG. 10 is a front, interior view of the embodiment of FIG. 9.

Moreover, in the embodiment of FIGS. 9 and 10, the actuation assembly 40' may also be configured to achieve a degree of sliding stability for the lancet 24. In this embodiment, a gear 30' protrudes from either one or both sides of the lancet 24 into movable engagement with one or more downwardly depending track segments 41 secured to the actuation assembly 40'. Interconnection and moveable engagement of the gear 30' with the gear tracks 41 and 28 cause the corresponding movement of the lancet 24 rearward into a compressed position from which it is subsequently released into the fired position.

Also, in the embodiment of FIGS. 9 and 10, a slot 68 may be provided within the lancet 24 so as to effectively receive the gear 30'. Of course, an open top or bottom configuration may also be effectively achieved, so long as the gear track 28 is appropriately positioned. Indeed, if desired the gear track 28 may be configured on the same side of the gear 30' as the actuation assembly 40'. However, in such a variation of this embodiment further modification of the actuation assembly 40' may be desired.

Further included in the embodiment of FIG. 9, is a restriction assembly which may comprise, in addition to or instead of biasing element 27 and abutment 33, abutment head 64' and housing abutment 65'. The actuation assembly 40' may thereby be locked in a position by interaction of the abutment elements 64' and 65' in a manner similar to that described with reference to the embodiment of FIG. 8, after it is been used to fire the lancet 24. Accordingly, whether positioned to the forward or rear end of the actuation assembly 40, 40', it is seen that a trigger lock assembly may be provided which can effectively achieve securement of the actuation assembly 40' and prevent intended and/or accidental re-use of the single use lancet device 10 of the present invention.

Figure 11:
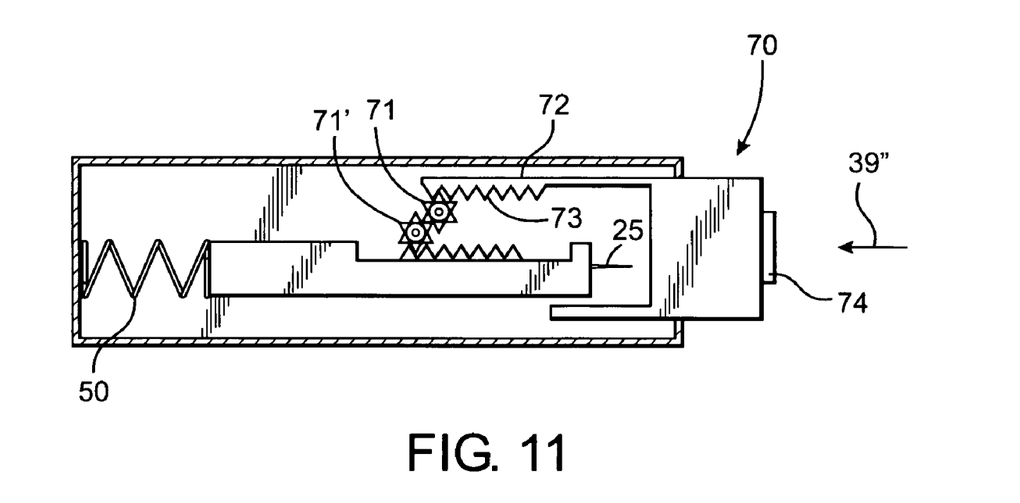
FIG. 11 is a side cross sectional view of yet another alternative embodiment of the single use lancet device of the present invention.

FIG. 11 represents yet another embodiment of the present invention, wherein the actuation assembly may be configured as a front push button, generally indicated as 70. In this embodiment, the front push button actuation assembly 70 includes at least an elongate element 72 mounted on the interior of the housing 20 and provided with a gear track 73 formed thereon. The gear track 73 is disposed and configured to movably engage and manipulate one or more gear elements of the positioning assembly. In the illustrated embodiment, the gear track 73 preferably engages an outer rotating gear element 71 of the positioning assembly, which in turn movably engages an inner rotating gear 71' of the positioning assembly, thereby changing the rotational direction of the inner rotating gear 71'. The inner gear 71' is further disposed in movable engaging relation with the gear track 28 disposed on the lancet 24. Accordingly, rearward movement of the push button actuation assembly 70 and the gear track 72, in accordance with directional arrow 39", causes the appropriate rearward movement of the lancet 24 due to the interconnection of the outer gear 71, the inner gear 71', and both gear tracks, 73 and 28. The lancet 24 is thereby compressed against the biasing element 50 of the driving assembly and is then subsequently released once free rotation of the positioning assembly results when the gear track 73 terminates and no longer engages the outer gear 71. The release of the lancet 24 results in the firing of the lancet 24 under the power of the biasing element 50. Moreover, the front push button actuation assembly 70 also includes a tab 74 that must be removed so the piercing tip 25 can pass through an aperture in the push button actuation assembly 70 when the lancet 24 is in its piercing orientation.

In addition, at least some if not all of the embodiments of the present invention include the side track or wing 26 preferably disposed and structured to achieve stability for the lancet 24 during the movement thereof.

Since many modifications, variations and changes in detail can be made to the described preferred embodiment of the invention, it is intended that all matters in the foregoing description and shown in the accompanying drawings be interpreted as illustrative and not in a limiting sense.

What is claimed is:

1. A single use lancet assembly comprising:
   a) a housing,
   b) a lancet movably disposed within said housing and including a piercing tip,
   c) an actuation assembly movably disposed in driving engagement with said lancet,
   d) at least one positioning member disposed to at least temporarily operatively interconnect said actuation assembly and said lancet,
   e) said actuation assembly structured to position said lancet at least temporarily into a cocked orientation upon actuation thereof concurrent with said positioning member engaging said lancet,
   f) a driving assembly drivingly engaging said lancet,
   g) said actuation assembly further structured to effect disengagement with said lancet upon continued actuation thereof after said lancet is disposed in said cocked orientation, and
   h) said driving assembly structured to move said lancet at least temporarily into a piercing orientation upon said disengagement with said lancet.

2. A single use lancet device as recited in claim 1 wherein said positioning member is structured to disengage said actuation assembly in order to effectuate said disengagement between said actuation assembly and said lancet.

3. A single use lancet device as recited in claim 1 wherein said positioning member comprises at least one gear element structured to engage a gear track on said actuation assembly.

4. A single use lancet device as recited in claim 3 further comprising at least two of said gear elements disposed in engaging relation with one another and interconnecting said actuation assembly and said lancet so as to effectuate rearward movement of said lancet upon rearward movement of said actuation assembly.

5. A single use lancet device as recited in claim 1 wherein said actuation assembly comprises an aperture defined therein through which said piercing tip of said lancet may pass.

6. A single use lancet device comprising:
   a) a housing,
   b) a lancet movably disposed within said housing and including a piercing tip,
   c) an actuation assembly movably mounted on said housing in driving relation to said lancet,
   d) a positioning assembly movably and releasably interconnecting said actuation assembly and said lancet,
   e) said positioning assembly comprises two movably interconnected gear members structured to inwardly move said lancet upon inward movement of said actuation assembly,
   f) a driving assembly disposed in driving engagement with said lancet and structured to move said lancet from a cocked orientation at least temporarily into a piercing orientation, and
   g) said piercing tip structured to extend through said actuation assembly subsequent to said lancet being disposed in said piercing orientation.

7. A lancet device as recited in claim 6 further comprising a restriction assembly disposed and structured to restrict movement of said lancet from said piercing orientation into said cocked orientation.

8. A lancet device as recited in claim 7 wherein said restriction assembly comprises at least one restrictor member and at least one stop member, said one restrictor member connected to one of said lancet or said actuation assembly and movable therewith, and said stop member fixedly secured to said housing and disposed in abutting relation to said one restrictor member as said lancet moves from said piercing orientation towards said cocked orientation.

* * * * *